US010359372B2

(12) United States Patent
Nyfors

(10) Patent No.: US 10,359,372 B2
(45) Date of Patent: Jul. 23, 2019

(54) CONDUCTIVITY MEASUREMENTS

(71) Applicant: Roxar Flow Measurement AS, Stavanger (NO)

(72) Inventor: Ebbe Gustaf Nyfors, Sandnes (NO)

(73) Assignee: Roxar Flow Measurement AS, Stavanger (NO)

( * ) Notice: Subject to any disclaimer, the term of this patent is extended or adjusted under 35 U.S.C. 154(b) by 0 days.

(21) Appl. No.: 14/654,773

(22) PCT Filed: Feb. 3, 2014

(86) PCT No.: PCT/EP2014/052036
§ 371 (c)(1),
(2) Date: Jun. 22, 2015

(87) PCT Pub. No.: WO2014/122093
PCT Pub. Date: Aug. 14, 2014

(65) Prior Publication Data
US 2015/0346117 A1    Dec. 3, 2015

(30) Foreign Application Priority Data
Feb. 5, 2013 (NO) .................................... 20130180

(51) Int. Cl.
*G01N 22/00* (2006.01)
*G01N 33/28* (2006.01)
*G01F 1/58* (2006.01)

(52) U.S. Cl.
CPC ............... *G01N 22/00* (2013.01); *G01F 1/58* (2013.01); *G01F 1/582* (2013.01); *G01N 33/2847* (2013.01)

(58) Field of Classification Search
CPC ....... G01N 22/00; G01N 33/28; A61B 5/0031
See application file for complete search history.

(56) References Cited

U.S. PATENT DOCUMENTS 4,745,617 A * 5/1988 Harvey .................. H01P 1/207
372/92
5,608,665 A * 3/1997 Wyszynski ............ H03H 11/04
708/300
(Continued)

FOREIGN PATENT DOCUMENTS

GB       2376074       12/2002
WO    WO-99063331 A2   12/1999
(Continued)

OTHER PUBLICATIONS

Ebbe Gustaf Nyfors, May 2000, Report S243, Cylindrical Microwave Resonator Sensors for Measuring Materials Under Flow.*
(Continued)

*Primary Examiner* — Giovanni Astacio-Oquendo
*Assistant Examiner* — Alvaro E Fortich
(74) *Attorney, Agent, or Firm* — Winstead PC

(57) ABSTRACT

The present invention relates to a system for measuring conductivity in a multiphase fluid flow comprising a fraction of water, the system comprising a measuring section including means for emitting electromagnetic signals into a pipe containing said flow within at least one chosen frequency range and means for detecting resonant frequencies within said range. The measuring section comprising features for providing at least two resonanct frequencies within said at least one frequency range, the system also comprising means for based on at least a first resonant frequency and a first Q-factor related to the corresponding resonance peak as well as the Q-factor of a second resonance peak, calculating the conductivity of the water in said flow.

14 Claims, 4 Drawing Sheets

(56) References Cited

U.S. PATENT DOCUMENTS

| | | | |
|---|---|---|---|
| 6,182,504 B1 | 2/2001 | Gaisford | |
| 6,351,409 B1* | 2/2002 | Rizzo | G11C 11/15 365/158 |
| 6,915,707 B2* | 7/2005 | Nyfors | G01F 1/40 73/861.63 |
| 8,224,588 B2* | 7/2012 | Wee | G01F 1/66 702/30 |
| 9,851,399 B2* | 12/2017 | Finkenzeller | G01R 31/315 |
| 2003/0122067 A1* | 7/2003 | Radtke | G01V 5/125 250/269.3 |
| 2004/0244501 A1* | 12/2004 | Nyfors | G01F 1/40 73/861.63 |
| 2007/0051685 A1* | 3/2007 | Wittmer | C02F 1/484 210/695 |
| 2008/0307860 A1* | 12/2008 | Guieze | G01F 1/7086 73/61.44 |
| 2009/0088985 A1* | 4/2009 | Wee | G01F 1/66 702/30 |
| 2009/0139345 A1* | 6/2009 | Xie | G01F 15/02 73/861.04 |
| 2009/0204346 A1* | 8/2009 | Xie | G01F 1/66 702/45 |
| 2010/0145636 A1* | 6/2010 | Nyfors | G01F 1/584 702/49 |
| 2010/0148804 A1* | 6/2010 | Jakoby | G01F 1/662 324/663 |
| 2011/0061475 A1* | 3/2011 | Guieze | G01N 1/2035 73/864 |
| 2011/0095772 A1* | 4/2011 | Sidhu | G01M 5/0033 324/693 |
| 2011/0118990 A1* | 5/2011 | Sidhu | G01B 7/16 702/35 |
| 2014/0216936 A1* | 8/2014 | Hughes | C02F 1/48 204/557 |

FOREIGN PATENT DOCUMENTS

| | | |
|---|---|---|
| WO | WO-03012413 A2 | 2/2003 |
| WO | WO-03034051 A1 | 4/2003 |
| WO | WO-2005057142 A1 | 6/2005 |
| WO | WO-2006019311 A1 | 2/2006 |
| WO | WO-2007018434 A1 | 2/2007 |
| WO | WO-2007129901 A1 | 11/2007 |
| WO | WO-2008085065 A1 | 7/2008 |
| WO | WO-2010115883 A1 | 10/2010 |

OTHER PUBLICATIONS

Nyfors, Ebbe Gustaf; "Cylindrical Microwave Resonator Sensors for Measuring Materials under Flow"; Dissertation for the degree of Doctor of Science in Technology, Report S243, Helsinki University of Technology; May 26, 2000; 181 pages.

Gilow, Christoph, "International Search Report," prepared for PCT/EP2014/052036, dated Apr. 22, 2014, four pages.

Wylie, S.R., et al., "RF Sensor for Multiphase Flow Measurement through an Oil Pipeline," Measurement Science & Technology, vol. 17, No. 8, Jul. 13, 2006, pp. 2141-2149.

* cited by examiner

CONDUCTIVITY MEASUREMENTS

This invention relates to a measuring system for measuring the characteristics of a fluid flow, especially a multiphase fluid flow comprising a fraction of water.

In oil and gas production and processing it is necessary to monitor the content and properties of the fluid flow as the fractions of oil, gas and water and the salinity of the water will change during the production and will affect the further processing. Several types of technology have been used to sample the information necessary to find the fractions and the salinity, such as acoustic measurements, pressure, gamma and electrical measurements. The present invention relates to electrical measurements used to determine the content in mixtures of oil, gas, and water and specifically the conductivity of the water of the flow, thus indicating the salinity and/or the water content in the flow. Dissolved salts in the water gives the water conductivity. The conductivity depends on the amount and type of ions in the solution, and the temperature. The water in a multiphase flow in the oil industry may contain several types of ions, but the by far most common arc $Na^+$ and $Cl^-$ from sodium chloride. By salinity we here mean the equivalent amount of sodium chloride, which gives the same conductivity as the actual solution, and it is expressed in % weight of the saline water.

As will be discussed below the solution according to the present invention use a microwave method which primarily provides a measure of the conductivity. The salinity can be calculated from the conductivity and the temperature using known models. In the same way the conductivity can any time be calculated from the salinity and the temperature using the same model in reverse.

In U.S. Pat. No. 6,182,504 a solution is discussed measuring the dielectric constant of the mixture as well as temperature, and then from these measurements decide whether the flow is water- or oil-continuous, and based upon this decision decide the type of measurements to be performed.

A method for measuring the multiphase flow is described in PCT application WO2005/057142. In this case the properties of the flow are measured as a function of the frequency of the electrical field applied through the transducers. The properties of the flow, or more precisely the electromagnetic loss and phase measurements, are measured in at least two directions in the flow, and the degree of annular flow is determined. The purpose of the solution disclosed in WO2005/057142 is thus to correct for measurement errors in specific flow regimes, mainly that of annular flow. It measures the cross section and closer to the wall to find out whether there is a difference.

In international application WO2007/018434, a solution is found for measuring the salinity/conductivity of the water in a multiphase flow. It is about measuring the differential phase shift at two or more frequencies with a transmission sensor made of three small antennas mounted in the pipe wall. This patent application is only related to measuring under water-continuous conditions.

In WO2006/019311 a method is described for measuring the salinity/conductivity of the water in a wet gas flow. This patent application relates to measuring the steepness of the phase response at the cut-off frequency. This is related to the losses caused by the conductivity, which are related to the salinity/conductivity. The problems with the method are related to the fact that the phenomenon is not monotonous, even though this is not mentioned in the patent, but shown here below.

In WO2008085065 a resonator is described which measures on the liquid film on the pipe wall in a wet gas flow. It is optimized for wet gas, i.e. very small amounts of water, and may become over-sensitive with multiphase flow.

One problem related to the known art discussed above is to obtain a measure of conductivity/salinity in an oil- or gas-continuous multiphase (including wet gas) flow so as to provide important information such as detection/measurement of formation water in wet gas, and for making a watercut or wet gas meter independent of changes in salinity.

As mentioned in U.S. Pat. No. 6,182,504 resonance may be used in relation to finding the conductivity in a flow. This is also described in and discussed in theory in Ebbe Gustaf Nyfors, "Cylindrical microwave resonator sensors for measuring materials under flow", Thesis for the degree of Doctor of Science in Technology, Report S243, May 2000, Helsinki University of Technology (ISBN 951-22-4983-9). As described in the thesis, a microwave resonator stores electromagnetic energy. In a measurement situation energy is fed into the resonance by the exciting source, and dissipated by various sources of losses. In the case of measuring a mixture containing water droplets, the currents induced in the droplets is one source of losses. Therefore the conductivity affects the resonance. A resonator has two main features, the resonant frequency and the Q-factor. Both are affected by the complex permittivity (also called dielectric constant). The fact that it is complex means that it has both a real and an imaginary part. The imaginary part is affected by the conductivity. With an oil- or gas-continuous mixture, which can be considered as a low-loss case (the imaginary part being far smaller than the real part) because the mixture is not conductive as a whole, the resonant frequency will depend mainly on the real part of the permittivity and the Q-factor also on the imaginary part.

The thesis also explains that microwave resonators can be described in terms of waveguide modes in transmission lines, like e.g. in hollow waveguides. A resonator can be formed either in a section bounded by two reflecting discontinuities (like grids, or a change of cut-off frequency) or by a hollow waveguide at cut-off, as explained below.

Electromagnetic energy can propagate in a hollow pipe (waveguide) as wave modes. Theoretically speaking a wave mode is a given field pattern, which is a specific solution to the electromagnetic problem in that environment, taking into account the boundary conditions (e.g. the electric field parallel to the metal wall must be zero at the surface). There are many solutions, i.e. wave modes. All wave modes in hollow pipes have one thing in common, they have a so-called cut-off frequency. This means that the wave mode can only propagate at frequencies higher than the cut-off frequency. But all modes have different cut-off frequencies.

If one makes a resonator into a pipe, and the resonant frequency is higher than the lowest cut-off frequency, the energy can escape and propagate away in the pipe (unless bounded by e.g. reflecting grids). This increases the losses of the resonator, i.e. the Q-factor becomes lower. Because the invention relates to measuring conductivity based on the losses it causes in a resonator, i.e. the conductivity reduces the Q-factor, it is easy to understand that the losses caused by radiation reduce the sensitivity and accuracy of the measurement. If on the other hand the resonant frequency is lower than the lowest cut-off frequency of the pipe, no energy can escape by radiation into the pipe and propagate away on a wave mode. Therefore the resonator structure can be relatively open (as the fin sensor as disclosed in WO99/063331) without causing extra losses reducing the Q-factor.

Another peculiar thing about wave modes is that the energy propagates with a velocity, which depends on the distance (in frequency) to the cut-off frequency. The closer to cut-off the slower they propagate. Exactly at the cut-off frequency they do not propagate at all. The wave mode is however excited or launched, but the energy stays where it is excited. This is in fact a resonance. I.e. each wave mode has a resonance at cut-off. This can also be used for measuring purposes. This resonance is, however, not a very good one. The peak has a given width, i.e. some distribution in the frequency domain. On the lower side of the top of the peak at the resonant/cut-off frequency the pipe provides radiation protection. On the upper side the energy can leak away, because the frequency is above cut-off. Therefore such a resonance peak is somewhat asymmetric, being steeper on the low-frequency side. It can, however, be used for measuring purposes. One way is to measure only the lower half, and then make a mirror image at the upper side to construct a whole peak. An advantage with this kind of resonator is that it is completely non-intrusive. Only some probes/antennas for coupling the energy are required. An example of a high-quality cut-off resonator is the above mentioned fin sensor. The resonance is a cut-off resonance at the cut-off of the section with the fin. In addition the resonator is bounded by sections without a fin, which have a higher cut-off frequency. The fact that is bounded (i.e. limited to the section with the fin) also has an effect on existence and location of the other resonance modes at higher frequencies, and is therefore relevant for the invention, as described below.

Thus a resonator sensor may be used for measuring complex permittivity under low-loss conditions and therefore a good solution. The conductivity affects the imaginary part of the permittivity, and will therefore affect the Q-factor of the resonator, e.g., as described in WO2003/034051. The problem is that the imaginary part of the permittivity of an oil- or gas-continuous mixture is not a monotonous function of the conductivity of the water. Therefore the change in the Q-factor is not monotonous as a function of the conductivity. Therefore the measurements are ambiguous. This is seen in practice, and predicted by the Bruggeman equation, which is an equation for calculating the permittivity of a mixture from the permittivities of the constituents and the volume fractions.

The ambiguity of the Q-factor as a function of conductivity, is as used in the system according to the present invention, a function of frequency. By performing the same measurement on two frequencies one can therefore solve the conductivity unambiguously, as will be discussed below.

Thus an additional object of the present invention is to provide a simplified measuring system for accurately and unambiguously monitoring the conductivity of the water in an oil- or gas-continuous multiphase or wet gas flow. This is performed using a measuring system as described in the following and being characterized as stated in the independent claims.

Thus the method and system according to the invention provides an improved measure of the conductivity in the flow by providing measurements at two resonant frequencies, the first resonant frequency providing information about the water content (watercut or water volume fraction) while the two Q-factors providing information also about the conductivity of the water. The two resonant frequencies may be in the same position and resonator, but may also be provided in two different resonators, e.g. having different cut-off frequencies such as in a pipe with two different diameters. Any sensor solution providing clear resonances in the flow may be used. Also, more than two resonant frequencies may be used.

The first resonant frequency may be close to the "cut-off frequency". Typically the wet gas meter or a watercut meter comprising a microwave fraction measuring system uses one resonant frequency to find the permittivity of the mixture. From the permittivity of the mixture, and the permittivities of the constituents, the mixing ratio, i.e. the fractions can be found. The Q-factor of the peak is affected by the losses due to conductivity in the water, but it is not unambiguous. But because the phenomenon is frequency dependent, one can get an unambiguous measurement of the conductivity by measuring the Q-factor of two peaks. I.e. one chooses a design such that two peaks are available. The resonant frequency of one is used for finding the fractions (watercut or water volume fraction) and the Q-factors of both to find the conductivity. This is a minimum. It is of course possible to make a correlation e.g. using neural networks making the connection between the resonant frequencies, Q-factors, and fractions and the conductivity. Of the two resonances one may be a cut-off type resonance (or even both, if the pipe diameter changes as in a venturi).

One of the resonances may or may not be a cut-off resonance, as described above. Actually both may be cut-off resonances, if the pipe diameter changes, e.g. one can be measured in the venturi throat, and the other in the larger pipe up- or down-streams of the venturi. The core in the invention is to measure the Q-factor of two resonances at different frequencies. From them the conductivity can be calculated. But generally the water content needs to be known, and roughly the frequencies for the Q-factors. Therefore a recommended procedure would be to measure both resonant frequencies and Q-factors, calculate the water content from one resonant frequency, and then the conductivity of the water from both peaks.

Any resonator has a peak in the insertion loss (i.e. the attenuation of the signal going through), when measured in transmission with two (or more) probes. In the same way any resonator displays a dip in the reflected power (return loss), when measured in reflection using only one probe.

It is also important to note that the frequency response of a resonator, whether measured in transmission or reflection, has both an amplitude (power) and a phase, as described in the thesis by Nyfors. Therefore the resonant frequency and Q-factor, or another parameter related to the losses (as e.g. steepness of the phase response), can also be determined by measuring the phase instead of the power, or both.

In the present specification "resonance peak" may also be understood as a "dip" in the spectrum, depending on the provided sensor and the term "Q-factor" also includes related variables such as peak width, related to the quality and definition of the resonance peak. Microwave is also to be understood in the broad sense essentially covering the range in the electromagnetic spectrum in which resonance is obtained in the flow. In addition the term WVF is used for water volume fraction, water cut or water content.

The invention will be described below with reference to the accompanying drawings, illustrating the invention by way of examples.

FIG. 1a illustrates the principal design of a conical insert in a pipe. Only one probe is shown, which is enough for measuring in reflection.

FIG. 1b illustrates the measured transmission frequency response of a typical conical insert as measured with two probes. The two first resonances are shown, which could be used for the invention. In this case both resonances belong to the same resonator.

Figure 6:
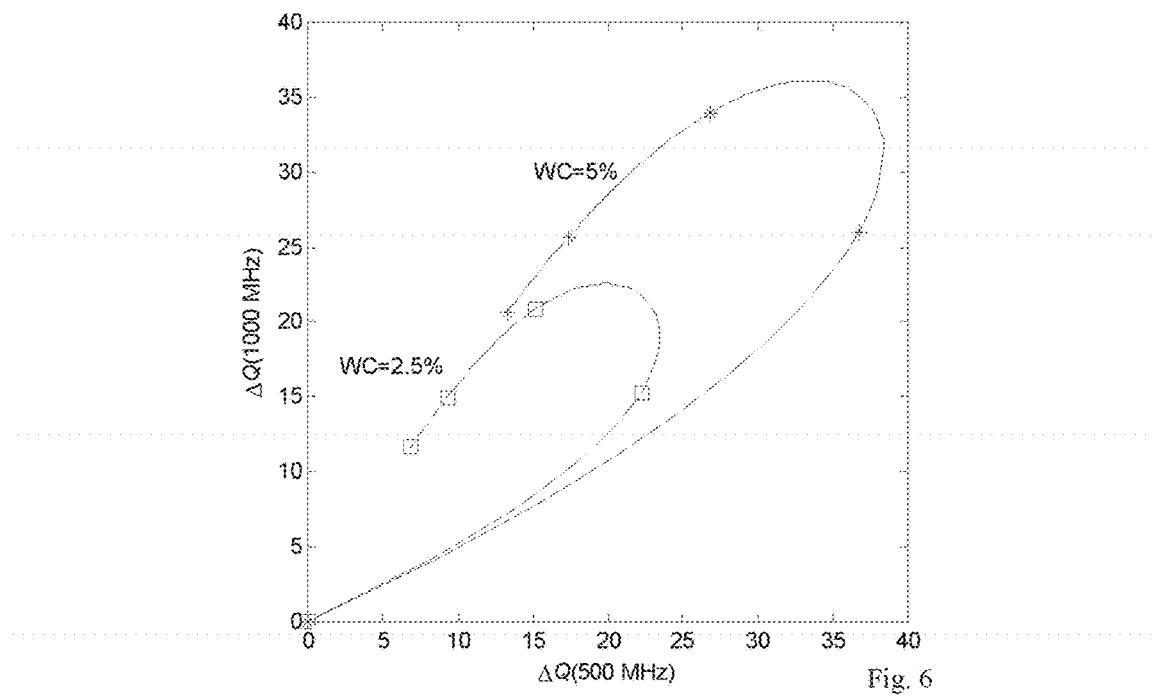

FIG. 6 illustrates the calculated change in Q at 500 MHz vs. at 1000 MHz caused by conductivity. The points indicate a salinity of 0, 1, 5, 10, and 15%. The temperature is 20° C.

Figure 1A:
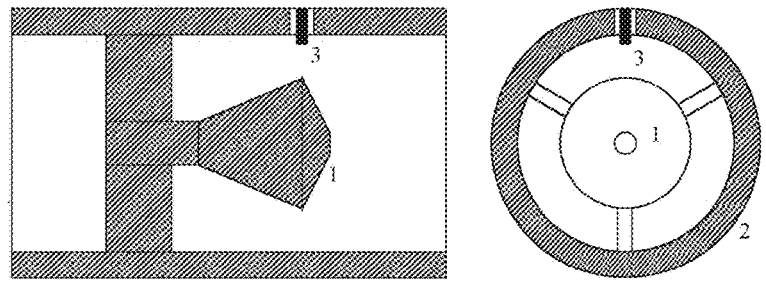
Figure 1B:
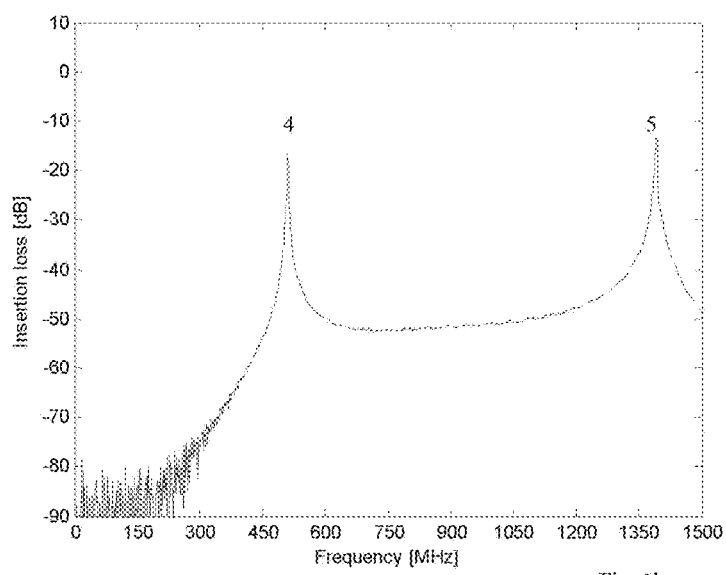

FIG. 1a illustrates a conical insert 1 used as a resonator in a pipe 2, as discussed in above-mentioned WO2010/115883 including a coupling device 3. The coupling device 3 may constitute a probe for applying the electromagnetic field and/or sensing the electromagnetic field for the purpose of determining the resonant frequency and the Q-factor. FIG. 1b illustrates the frequency response of a typical conical insert in a frequency range comprising two resonant frequencies 4,5. A typical pipe diameter may be in the range of 50 mm to 245 mm, but this may vary depending on the situation.

Figure 2A:
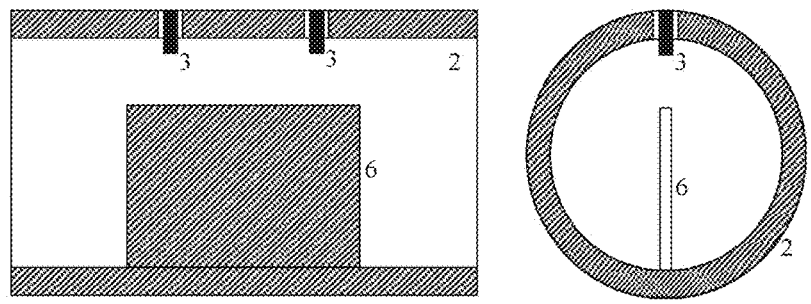
FIG. 2a illustrates the principal design of a fin resonator.
Figure 2B:
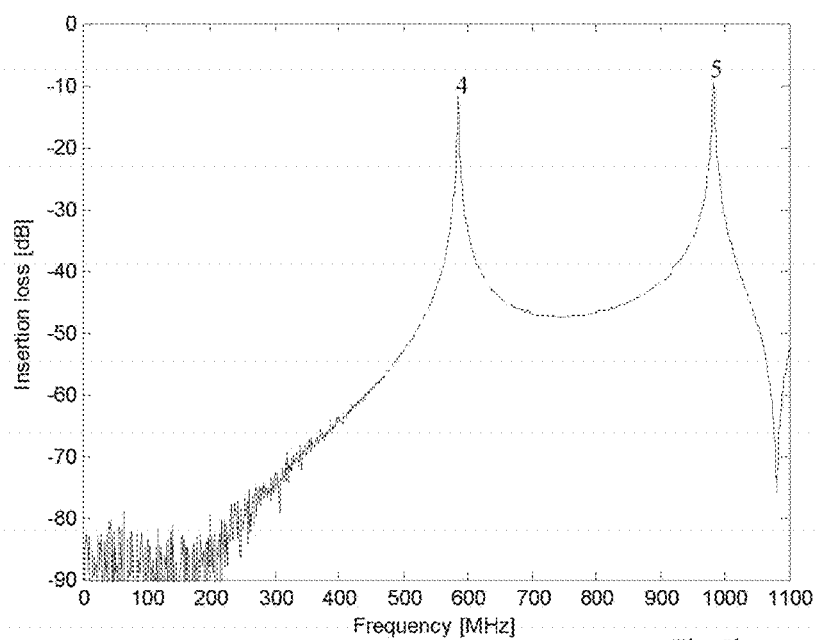
FIG. 2b illustrates the measured frequency response of a fin resonator, with the first two resonances shown, which could be used for the invention. In this case both resonances belong to the same resonator.

FIG. 2a illustrates an alternative resonator constituted by a fin 6 extending into the flow. FIG. 2b illustrates the two first resonance peaks in this configuration, based on an inner pipe diameter of 146.4 mm with a fin length of about one pipe diameter.

Figure 3:
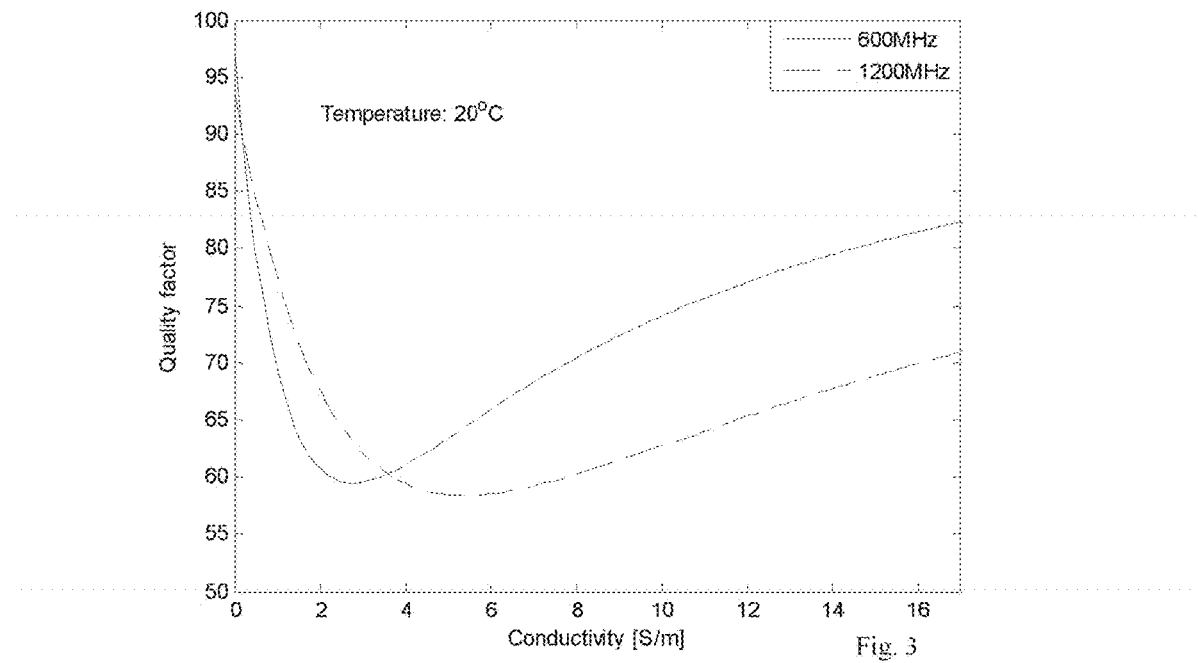
FIG. 3 illustrates an example using the Brüggeman equation for calculating the Q-factor for a mixture of diesel and water, WC=5%.

As will be obvious to a person skilled in the art, several configurations may be contemplated. A plain, unobstructed pipe will have a single resonant frequency at the cut-off frequency. It is, however, possible within the scope of the present invention to use two resonators at two different pipe diameters, each resonating at cut-off, comparing the Q-factors (or some other parameter related to the losses, as e.g. the peak width or the steepness of the phase response) for measuring the conductivity according to the invention. Resonance at cut-off will also have some extra loss due to radiation by propagation in the pipe on frequencies above the resonant frequency, i.e. in the right half of the peak resulting in an unsymmetric peak, which reduces the accuracy of the measurement of the Q-factor. Thus for high measurement accuracy preferably some structure should be provided providing a resonant frequency below the cut-off frequency, while a plain cut-off resonator as discussed above is attractive as being completely non-intrusive FIG. 3 illustrates an important aspect of the present invention as the measured Q-factor depends on the conductivity of the water in the flow as well as the resonant frequency. At any single frequency the change in the Q-factor due to conductivity is not monotonous. Thus the Q-factor can obtain the same value for two different values for the water conductivity. But because of the frequency dependence, measuring the Q-factor at two different frequencies will provide a unique measure of the conductivity of the water in the flow.

Figure 4:
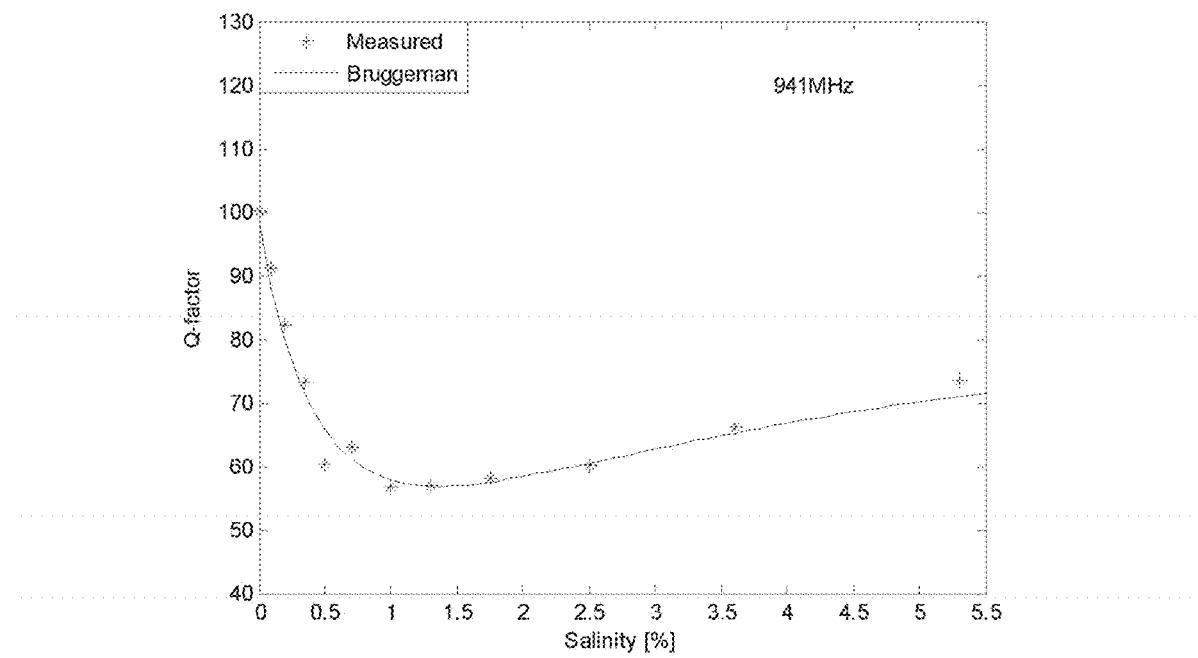
FIG. 4 illustrates the measured Q-factor of a coaxial resonator with a mixture of diesel and water (WC=5%) compared with that predicted using the Brüggeman equation. T=53.5° C.
Figure 5:
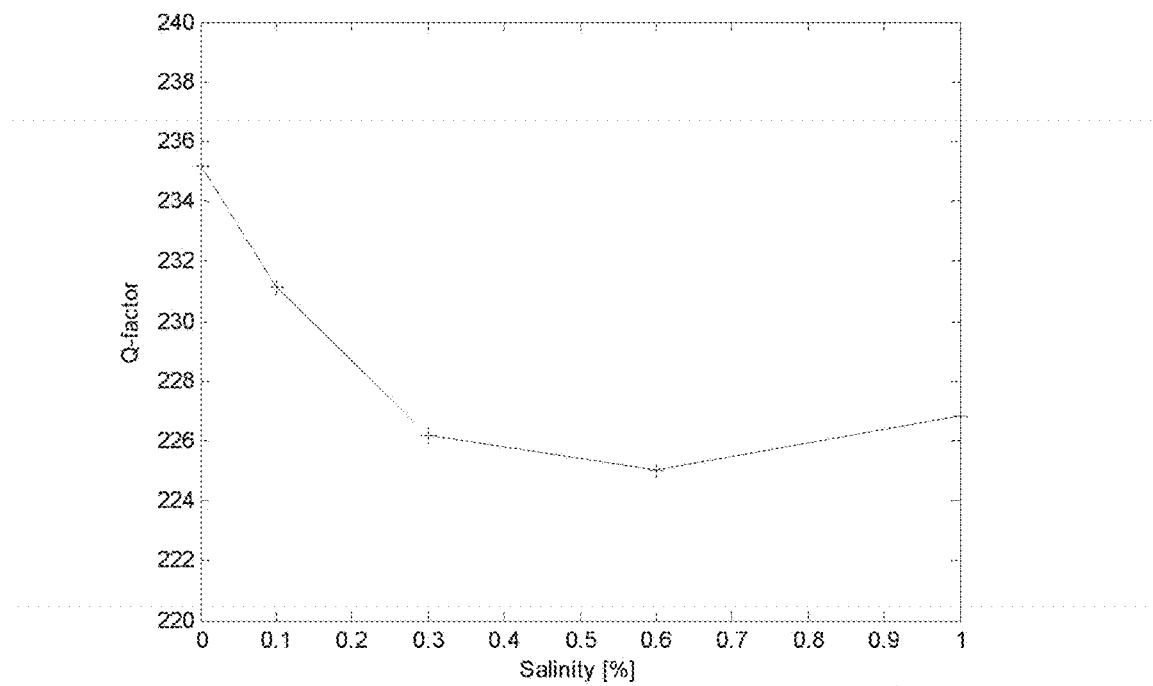
FIG. 5 illustrates the measured Q-factor in a wet gas flow as a function of salinity at a frequency of 300 MHz. The WVF (water volume fraction) was 0.1%, and the CVF (condensate volume fraction) was 0.332%.

This is also illustrated in FIGS. 4 and 5. In FIG. 4 the Q-factor is measured (*) and calculated (–) while varying the salinity of the water of a known mixture of diesel and water, at a resonant frequency of 941 MHz. In FIG. 5 the Q-factor in a wet gas flow is measured as a function of salinity at a frequency of 300 MHz. The WVF (water volume fraction) was 0.1%, and the CVF (condensate volume fraction) was 0.332%.

FIG. 6 illustrates a comparison between two sets of measurements at two resonance frequencies, 500 MHz and 1000 MHz, with salinities of 0, 1, 5, 10, and 15%, counter-clockwise starting a 0%, with watercut 2.5% and 5%. The change in Q-factor ΔQ at 500 MHz and 1000 MHz between the salinities at two watercut ratios defined different curves and thus by knowing the watercut the salinity may also be found.

The resonant frequency is affected primarily by the watercut or the WVF, but also as a secondary effect by the salinity. Therefore the salinity or the water conductivity is normally given as a manual input through the user interface in watercut or wet gas meters. If the salinity varies over time, which may happen of a variety of reasons, this will affect the accuracy of the readings. Therefore the ability of the meter to measure the salinity as according to the invention will provide a higher accuracy for the watercut or WVF measurement, and especially to maintain the accuracy over time as the salinity changes. And in addition the salinity is important information as such, and therefore an important output parameter as an extra feature of a watercut or wet gas meter. Especially with wet gas, the salinity is an indicator of the production of formation water, which is very important information. But regarding the retrieval of the salinity and the watercut or WVF: Each point in the diagram defines a unique combination of watercut or WVF and conductivity. Therefore prior knowledge of the watercut/WVF is not needed to be able to calculate the conductivity. I.e. one will get both from just the Q-factors. On the other hand, the resonant frequency will give a more accurate measure of the watercut/WVF. Therefore a recommended practice would be to derive a first estimate for the watercut/WVF from the resonant frequency of one of the peaks and the conductivity from the Q-factors, then calculate a more accurate watercut/WVF from the resonant frequency, then improve the conductivity result, etc. Thus an iterative process would give the highest accuracy for both.

To summarize the system according to the invention thus relates to a system for measuring conductivity of the water in fluid flows constituted by oil- or gas-continuous mixtures comprising a measuring section including means for emitting electromagnetic signals into a pipe containing said flow within at least one chosen frequency range and means for detecting resonance frequencies within said range. The measurement is preferably performed by transmitting a frequency sweep into said pipe and measuring the response to provide information about the resonant frequencies and Q-factors. Q-factors according to the present invention may also be understood as including the phase response or peak width without directly calculating the Q-factor value.

The measuring section comprising features for providing at least two resonant frequencies within said at least one frequency range. The system also comprising means for based on at least one of the resonance frequencies, a first Q-factor related to the corresponding resonance peak as well as the Q-factor of a second resonance peak, calculating the conductivity of the water of said flow. The calculations thus being based on minimum one measured resonant frequency and two Q-factors. The second resonant frequency may optionally also be determined in order to increase the accuracy.

The measuring section may preferably comprise an insert or other structure in said flow, which results in a resonant frequency which is lower than the cut-off frequency of the pipe or the cut-off frequency in each end of the measuring section, and thus may allow the structure to be relatively open and little intrusive, and still have a high Q-factor. A high Q-factor (i.e. low total losses) enables a high sensitivity to the losses caused by the conductivity in the water. The insert may be chosen from a wide range of structures such as a conical insert, fin or any structure providing a defined reflection at two locations (such as two metal grids, or other open- or short-circuited ends of a transmission line structure, like the open end and the end shorted by the legs of the conical insert, or the ends of the fin) so as to obtain a resonance between the reflecting locations. Two different resonant frequencies may be obtained by two structures having two different resonant frequencies or preferably by providing an insert giving two resonant frequencies within the emitted frequency range. More than two resonanct frequencies and Q-factors may also be utilized.

The measurement section may also preferably comprise a plain pipe, as discussed above, in which case it is a cut-off resonator. This structure is preferable if non-intrusiveness is the highest priority. By analogy with the reflecting points in resonators formed by inserts, the opposite sides of the pipe form the reflecting points as the propagation at the cut-off frequency is purely radial. Because the invention requires a minimum of two resonances, a cut-off resonator must be combined with either another cut-off resonator, where the pipe diameter is different (as in the venturi throat), a resonator based on another structure (such as an insert), or another wave mode may be used. Because a waveguide can support a number of different wave modes, which all have different cut-off frequencies, it is possible to use two different cut-off resonances in the same pipe. Care must then be taken in the choice of modes and the choice of type and location of coupling devices so that power will not leak from the mode with the higher cut-off frequency to the one with the lower cut-off frequency. It may be preferable to use separate coupling devices for the minimum two modes. They can then be mounted at locations, where the other mode has zero electric field, and therefore only couple to the desired mode.

The calculation comprises a comparison between said measured values and an at least partially empirical model based on a known measuring situation stored in the system. Alternatively the calculation of resonant frequency and Q-factors is performed in a neural network model, thus relating to a model found and stored by the computer as a result of previous measurements and/or a predetermined model. The resonant frequencies and Q-factors would normally be calculated first in the "normal" way from the measured frequency response/sweep. Then a neural network or multivariate analysis-based model could be used for finding the conductivity of the water. It may also be contemplated to directly input the raw measurements, without calculating the resonant frequencies and Q-factors at all.

The detection of the resonance (the resonant frequency and Q-factor) may be performed by different types of measurements, as for example discussed in chapter 3 in the Nyfors report or other of the referred documents, and will not be discussed in detail here. The determination of each Q-factor is also per se known, e.g. from the abovementioned publications.

The invention claimed is:

1. A system for measuring conductivity in a multiphase fluid flow comprising a fraction of water, the system comprising:
   a measuring section including a coupling device, wherein the coupling device is configured to:
      emit electromagnetic signals into a pipe containing said flow within at least one chosen frequency range;
      detect resonances within said range;
   wherein the measuring section is exposed to the multiphase fluid flow and comprises features for providing at least two resonances within said at least one frequency range;
   wherein the features comprise an insert for forming a transmission line along which electromagnetic waves can propagate and be reflected from ends resulting in a series of resonances; and
   based on at least a first resonant frequency and a first Q-factor related to a corresponding resonance peak and the Q-factor of a second resonance peak, the conductivity of the water is calculated in said flow by a comparison between measured values and a model stored in the system, the model being an at least partially empirical model based on a known measuring situation or a neural network model based on a model found and stored by a computer as a result of at least one of previous measurements and a predetermined model, thereby enabling the system to provide information about the water content through the first resonance frequency while the two Q-factors provide information about the conductivity of the water.

2. The system according to claim 1, wherein a second resonant frequency of the at least two resonances is detected.

3. The system according to claim 1, wherein calculation of conductivity is performed in a neural network model.

4. The system according to claim 1, wherein calculation of resonant frequency and Q-factors is performed in a neural network model.

5. The system according to claim 1, wherein the insert is constituted by end grids, which provide shorted ends to electromagnetic waves, but allow flow to pass.

6. The system according to claim 1, wherein the at least one of said resonators is below a lowest cut-off frequency on the pipe.

7. The system according to claim 1, wherein the insert is a cone or fin defining a resonator in the pipe.

8. A system for measuring conductivity in a multiphase fluid flow comprising a fraction of water, the system comprising:
   a measuring section including a coupling device, wherein the coupling device is configured to:
      emit electromagnetic signals into a pipe containing said flow within at least one chosen frequency range;
      detect resonances within said range;
      wherein the measuring section is exposed to the multiphase fluid flow and comprises features for providing at least two resonances within said at least one frequency range;
   the features including a change in pipe diameter for providing at least two different cut-off resonances; and
   based on at least a first resonant frequency and a first Q-factor related to a corresponding resonance peak and the Q-factor of a second resonance peak, the conductivity of the water is calculated in said flow by a comparison between measured values and a model stored in the system, the model being an at least partially empirical model based on a known measuring situation or a neural network model based on a model found and stored by a computer as a result of at least one of previous measurements and a predetermined model, thereby enabling the system to provide information about the water content through the first resonance frequency while the two Q-factors provide information about the conductivity of the water.

9. The system according to claim 8, including means for measuring phase response in a range around each resonant frequency, wherein the first Q-factor and the second Q-factor are calculated from the measured slope of the phase response.

10. The system according to claim 8, wherein:
both measuring sections provide resonance at a cut-off frequency; and
the first measuring section is in the pipe and the second measuring section is in a restriction or an enlargement.

11. The system according to claim 10, wherein the restriction is a venturi throat.

12. A system for measuring conductivity in a multiphase fluid flow comprising a fraction of water, the system comprising:
a measuring section including a coupling device, wherein the coupling device is configured to:
emit electromagnetic signals into a pipe containing said flow within at least one chosen frequency range;
detect resonances within said range;
wherein the measuring section is exposed to the multiphase fluid flow and comprises features for providing at least two resonances within said at least one frequency range;
the features including a section of pipe providing a cut-off resonance and an insert forming a transmission line along which electromagnetic waves can propagate and be reflected from the ends resulting in at least one other resonance; and
based on at least a first resonant frequency and a first Q-factor related to a corresponding resonance peak and the Q-factor of a second resonance peak, the conductivity of the water is calculated in said flow by a comparison between measured values and a model stored in the system, the model being an at least partially empirical model based on a known measuring situation or a neural network model based on a model found and stored by a computer as a result of at least one of previous measurements and a predetermined model, thereby enabling the system to provide information about the water content through the first resonance frequency while the two Q-factors provide information about the conductivity of the water.

13. The system according to claim 12, wherein at least one of said resonances is at a lowest cut-off frequency of said pipe.

14. The system according to claim 12, comprising a first measuring section and a second measuring section, each including means for emitting electromagnetic signals into a pipe containing said flow within at least one chosen frequency range and means for detecting resonance frequencies within said at least one chosen frequency range, the two measuring sections having different resonant frequencies, a first and a second Q-factor being found for the first measuring section and the second measuring section.

* * * * *